(12) United States Patent
Lu et al.

(10) Patent No.: US 10,074,037 B2
(45) Date of Patent: Sep. 11, 2018

(54) SYSTEM AND METHOD FOR DETERMINING OPTIMAL OPERATING PARAMETERS FOR MEDICAL IMAGING

(71) Applicant: Siemens Healthcare GmbH, Erlangen (DE)

(72) Inventors: Xiaoguang Lu, West Windsor, NJ (US); Vibhas Deshpande, Austin, TX (US); Peter Kollasch, Minnetonka, MN (US); Dingxin Wang, Apple Valley, MN (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 131 days.

(21) Appl. No.: 15/172,949

(22) Filed: Jun. 3, 2016

(65) Prior Publication Data

US 2017/0351937 A1 Dec. 7, 2017

(51) Int. Cl.
| | |
|---|---|
| *G06K 9/00* | (2006.01) |
| *G06K 9/62* | (2006.01) |
| *A61B 5/055* | (2006.01) |
| *A61B 5/00* | (2006.01) |
| *A61B 6/03* | (2006.01) |
| *A61B 8/00* | (2006.01) |
| *G06N 99/00* | (2010.01) |
| *G06T 7/00* | (2017.01) |
| *G01R 33/54* | (2006.01) |

(52) U.S. Cl.
CPC ............ *G06K 9/6265* (2013.01); *A61B 5/055* (2013.01); *A61B 5/4585* (2013.01); *A61B 6/032* (2013.01); *A61B 6/037* (2013.01); *A61B 8/58* (2013.01); *G01R 33/543* (2013.01); *G06N 99/005* (2013.01); *G06T 7/0014* (2013.01); *G06T 2207/30048* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 6,907,144 B1 * | 6/2005 | Gindele | G06T 5/20 382/262 |
| 7,248,749 B2 * | 7/2007 | Avinash | G06T 5/002 382/260 |
| 7,639,010 B2 | 12/2009 | Park | |
| 7,649,353 B2 | 1/2010 | Feiweier et al. | |
| 7,821,266 B2 | 10/2010 | Feiweier | |

(Continued)

OTHER PUBLICATIONS

Schölkopf et al., "New Support Vector Algorithms," Neural Computation 12 (2000), pp. 1207-1245.

(Continued)

*Primary Examiner* — Nancy Bitar

(57) ABSTRACT

Systems and methods for determining optimized imaging parameters for imaging a patient include learning a model of a relationship between known imaging parameters and a quality measure, the known imaging parameters and the quality measure being determined from training data. Optimized imaging parameters are determined by optimizing the quality measure using the learned model. Images of the patient are acquired using the optimized imaging parameters.

21 Claims, 6 Drawing Sheets

(56) References Cited

U.S. PATENT DOCUMENTS

| | | | | |
|---|---|---|---|---|
| 8,433,472 B2* | 4/2013 | Singh | G05B 23/024 | |
| | | | 701/31.4 | |
| 8,975,892 B2 | 3/2015 | Flammang et al. | | |
| 9,292,801 B2* | 3/2016 | Fujimaki | G06N 99/005 | |
| 9,418,119 B2* | 8/2016 | Liu | G06F 17/30598 | |
| 2005/0025377 A1* | 2/2005 | Avinash | G06T 5/002 | |
| | | | 382/260 | |
| 2008/0292194 A1* | 11/2008 | Schmidt | G06T 7/0012 | |
| | | | 382/217 | |
| 2011/0123100 A1* | 5/2011 | Carroll | G06F 19/3437 | |
| | | | 382/155 | |
| 2014/0021357 A1* | 1/2014 | Wang | G06T 5/003 | |
| | | | 250/363.01 | |
| 2015/0016701 A1 | 1/2015 | Jog et al. | | |
| 2015/0071514 A1 | 3/2015 | Wang et al. | | |
| 2015/0199478 A1* | 7/2015 | Bhatia | A61B 6/488 | |
| | | | 382/128 | |

OTHER PUBLICATIONS

Chang et al., "LIBSVM: a Library for Support Vector Machines," ACM Transactions on Intelligent Systems and Technology 2 (3), Last updated: Jan. 3, 2006, pp. 1-22.

Byrd et al., "A Trust Region Method Based on Interior point Techniques for Nonlinear Programming," Math. Program., No. 1, vol. 89 (2000), pp. 149-185.

Lindstrom Anton et al: "Bone contrast optimization in magnetic resonance imaging using experimental design of ultra-short echo-time parameters", Chemometrics and Intelligent Laboratory Systems, Elsevier Science Publishers B.V. Amsterdam, NL, vol. 125, Mar. 29, 2013 (Mar. 29, 2013); pp. 33-39.

Charles Q. Li et al: "Optimizing isotropic three-dimensional fast spin-echo methods for imaging the knee : Optimizing Isotropic 3D FSE Knee MRI", Journal of Magnetic Resonance Imaging, vol. 39, No. 6, Jun. 1, 2014 (Jun. 1, 2014); pp. 1417-1425.

Extended European Search Report dated Dec. 14, 2017 in corresponding European application No. 17173775.2.

\* cited by examiner

SYSTEM AND METHOD FOR DETERMINING OPTIMAL OPERATING PARAMETERS FOR MEDICAL IMAGING

BACKGROUND OF THE INVENTION

The present invention relates generally to medical imaging, and more particularly to determining optimal operating parameters for medical imaging.

Medical imaging is a crucial tool to support diagnoses and is widely accepted in clinical applications. To generate clinically acceptable images, a number of scanner, patient, and examination parameters need to be set before an exam or procedure is performed. For example, in magnetic resonance imaging (MRI) knee exams, repetition time (TR), echo time (TE), and other parameters need to be determined prior to the exam. In current clinical practice, these parameters are manually adjusted by a technician or operator based on their experience and individual choice. However, the number of possible values for these parameters is large and includes values or combinations of values that deliver poor quality images. Adjusting these combinations of parameters to generate clinically acceptable images is prohibitive with logical evaluation because of the large number of possible combinations. Moreover, with the variety of equipment in a facility, or after changes to a system such as software or hardware upgrades, the burden of changing the practices to state-of-the-art are cumbersome at best and inefficient due to their manual nature.

BRIEF SUMMARY OF THE INVENTION

In accordance with an embodiment, systems and methods for determining optimized imaging parameters for imaging a patient include learning a model of a relationship between known imaging parameters and a quality measure, the known imaging parameters and the quality measure being determined from training data. Optimized imaging parameters are determined by optimizing the quality measure using the learned model. Images of the patient are acquired using the optimized imaging parameters.

In accordance with an embodiment, determining optimized imaging parameters by optimizing the quality measure using the learned model includes maximizing the quality measure.

In accordance with an embodiment, the quality measure includes at least one of a signal-to-noise ratio, a contrast-to-noise ratio, a resolution, a measure of motion artifacts, and a measure of ghosting. The quality measure may be selected based on a procedure being performed. The signal-to-noise ratio may be determined as a ratio between an average intensity value of pixels in a first region of interest in a target structure in an image and an average intensity value of pixels in a second region of interest outside of the target structure in the image.

In accordance with an embodiment, the known imaging parameters include parameters for operating an image acquisition device.

In accordance with an embodiment, the optimized imaging parameters are constrained to be within a range of the known imaging parameters.

In accordance with an embodiment, optimizing the quality measure includes optimizing the quality measure using an interior point algorithm.

In accordance with an embodiment, learning the model includes learning the model using a regression analysis.

These and other advantages of the invention will be apparent to those of ordinary skill in the art by reference to the following detailed description and the accompanying drawings.

DETAILED DESCRIPTION

The present invention generally relates to a data-driven learning based approach to determine optimal operating parameters for medical imaging scanners. Embodiments of the present invention are described herein to give a visual understanding of methods for learning-based aorta segmentation. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

While the embodiments discussed herein may be discussed in terms of medical imaging of a patient for medical procedures, the embodiments discussed herein are not so limited. It should be understood that the embodiments discussed herein may be applied for imaging of any subject for any procedure.

Figure 1:
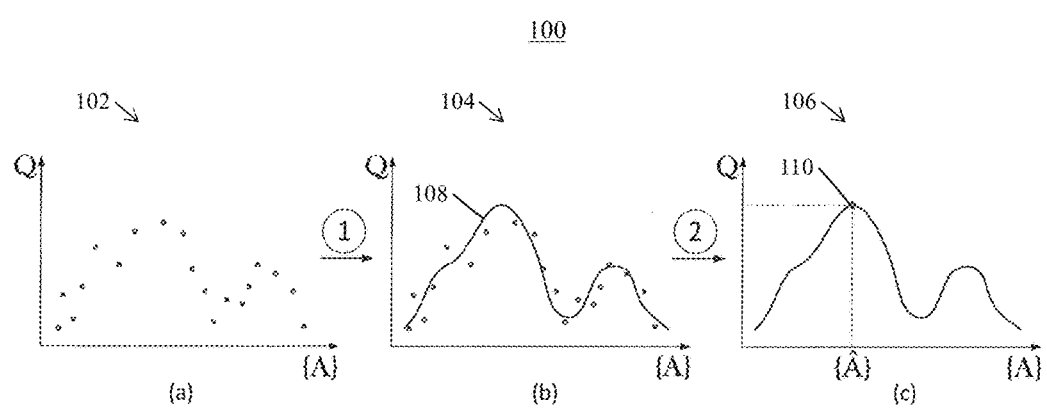
FIG. 1 shows a workflow for determining parameters for medical imaging, in accordance with one embodiment.

FIG. 1 shows a workflow 100 for determining parameters for medical imaging, in accordance with one or more embodiments. Workflow 100 includes graph 102 where training data is plotted to compare a set of parameters $\{A\}$ with a corresponding quality measure Q. As shown in graph 102, the quality measure Q is dependent on the values of the set of parameters $\{A\}$. The parameters may be parameters of an imaging device (e.g., repetition time and echo time), parameters of the patient, parameters of the exam, etc. Note that in graph 102, axis $\{A\}$ represents a multi-dimensional space instead of a one-dimensional space. From graph 102, a mapping $\phi$ 108 is learned of the relationship between the set of parameters $\{A\}$ and the quality measure Q in graph 104. The dependency between Q and $\{A\}$ is modelled by following an underlying mapping $\phi:\{A\} \to Q\{R'' \to R\}$. The mapping $\phi$ 108 may be learned using a support vector regression algorithm. In graph 106, the quality measure Q is optimized 110 (e.g., maximized) within the range of the set of parameters $\{A\}$ to provide an optimized set of parameter values $\{\hat{A}\}$ (or range of values) that is expected to generate good quality images. Optimization may be performed by applying an interior point algorithm. Optimal parameters for medical imaging are determined as the parameters corresponding to the optimized quality measure Q from the mapping ϕ 108.

Figure 2:
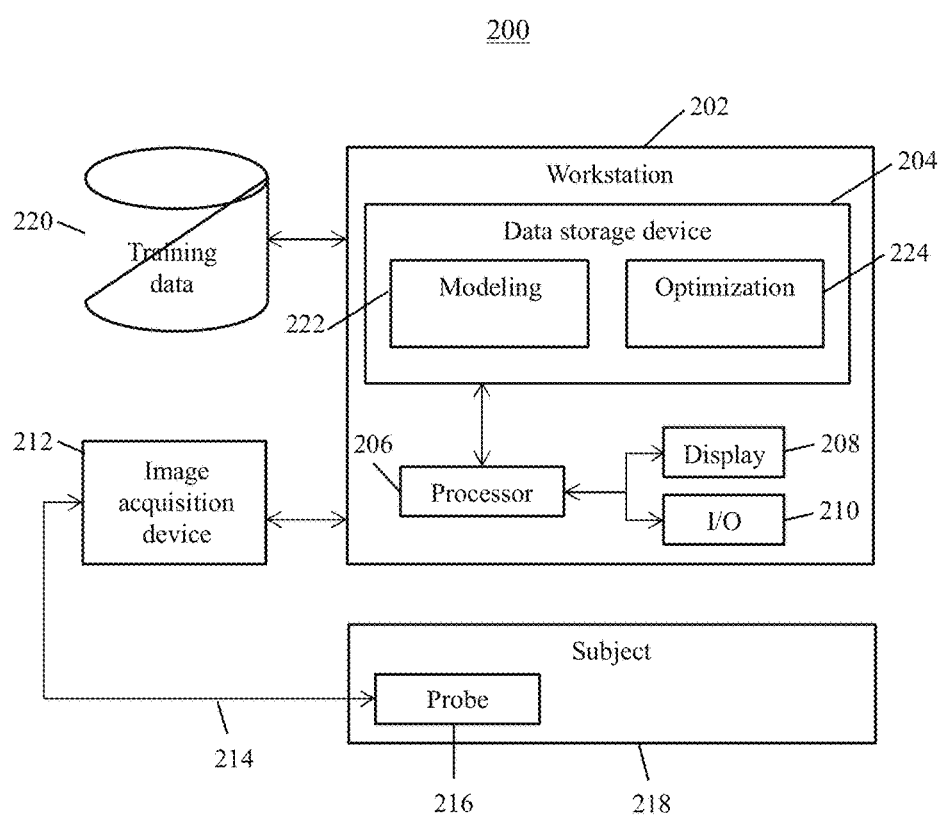
FIG. 2 shows a system for determining parameters for medical imaging, in accordance with one embodiment.

FIG. 2 shows a system 200 for determining parameters for medical imaging, in accordance with one or more embodiments. System 200 includes workstation 202, which may be used for assisting a user (e.g., a clinician) during a procedure, such as, e.g., a patient examination. Workstation 202 includes one or more processors 206 communicatively coupled to data storage device 204, display device 208, and input/output devices 210. Data storage device 204 stores a plurality of modules representing functionality of workstation 202 performed when executed on processor 206. It should be understood that workstation 202 may also include additional elements, such as, e.g., a communications interface.

Workstation 202 may assist the clinician in imaging subject 218, such as, e.g., a patient, for a medical procedure. Workstation 202 may receive medical imaging data of subject 218 from image acquisition device 212. Image acquisition device 212 may be of any modality, such as, e.g., magnetic resonance imaging (MRI), computed tomography (CT), ultrasound (US), single-photon emission computed tomography (SPECT), positron emission tomography (PET), or any other suitable modality or combination of modalities.

In some embodiments, image acquisition device 212 may employ one or more probes 216 for imaging subject 218. Probe 216 may be instrumented with one or more devices (not shown) for performing the procedure. The devices instrumented on probe 216 may include, for example, imaging devices, tracking devices, insufflation devices, incision devices, and/or any other suitable device. Image acquisition device 212 is communicatively coupled to probe 216 via connection 214, which may include an electrical connection, an optical connection, a connection for insufflation (e.g., conduit), or any other suitable connection.

To generate clinically acceptable images from image acquisition device 212, a number of parameters must be set before an exam is performed. The parameters may include, e.g., parameters of image acquisition device 212, parameters of subject 218, parameters of the procedure, etc. For example, in an MRI knee exam, the parameters of the MRI imaging device may include repetition time (TR) and echo time (TE). In another example, the parameters may include patient positioning and coil positioning. System 200 provides optimal operating parameters using a learning-based approach by first modeling or mapping the dependencies between the parameters and a quality measure based on training data 220, and then by optimizing the quality measure using the mapping to provide a range of values for the set of parameters that are predicted to deliver good quality images. In some embodiments, the parameters may include parameters that are used for learning the model but are not provided as the optimal operating parameters. For example, these parameters may include physiology parameters of subject 218 such as weight.

Modeling module 222 is configured to build or learn a mapping ϕ between a set of parameters {A} and a quality measurement Q from training data 220. Modeling module 222 employs a regression analysis to learn the mapping ϕ between the set of parameters {A} and the quality measurement Q, which are annotated in training data 220. In one embodiment, a support vector regression (SVR) algorithm is employed. Other types of regression analysis may also be employed.

Training data 220 is received by workstation 202. Training data 220 is acquired prior to the procedure and may be of the same patient 118 or a different patient or set of patients. Training data 220 includes training images that are annotated to provide the set of parameters {A} and the corresponding values for the quality measure Q. The quality measure Q may be any measure representing the quality of images for a particular application and may be defined based on the procedure being performed. In one particularly useful embodiment, the quality measure Q is defined as the signal-to-noise ratio (SNR) for optimizing image quality. However, it should be understood that the embodiments discussed herein are not limited to the traditional image quality measurement as its optimization target. Rather, the embodiments discussed herein may be applicable to optimizing imaging to various metrics of success. For example, if an MR scan is being acquired to detect lesions, then the quality measure Q may be defined to characterize the ability to detection lesions. While the image quality may traditionally be considered poor in this example, it could suffice for the diagnostic task that the scan is being performed for. Other examples of the quality measure Q may include, for example, a contrast-to-noise ratio (CNR), a resolution, a measure of motion artifacts, a measure of ghosting, qualitative clinical diagnostic image quality measures, or any other suitable quality measure or combination of quality measures. In one embodiment, the quality measure Q is a combination of multiple metrics represented as a single objective function. For example, in one embodiment, multiple quality metrics may be combined through a normalized summary, where each individual quality metric is first normalized into a range that can be compared with each other (e.g., [0 1]), then a summation is performed to add all normalized measures.

Optimization module 224 is configured to optimize the quality measure Q based on the learned model ϕ. Optimization module 224 may employ any suitable algorithm, such as, e.g., an interior point algorithm. In one embodiment, optimization module 224 maximizes the quality measure Q. An optimized set of parameter values {Â} corresponding to the optimized quality measure is selected using the learned model ϕ to generate good quality images. The optimized set of parameter values {Â} is constrained by the feasible value range of the set of parameters {A} of training data 220. Optimization module 224 outputs the optimized set of parameter values {Â} for performing the procedure. The optimized set of parameter values {Â} may be used for acquiring images of a patient.

Advantageously, system 200 provides for a data-driven approach without using handcraft models, which have difficulty capturing the large complexity presented in determining optimized operating parameters. Complex collective impact on image quality with the parameters in combination is taken into account during the modeling process. The derived model or mapping forms a large collective database and is expected to deliver more consistent image quality and ensure a high success rate of exams irrespective of scanner types, hardware variances, software variances, operators, local conditions, etc.

In one experiment, 38 knee exams were collected using an MRI scanner. From each exam, the sagittal series was extracted, which included approximately 30 slices. Along with each series, acquisition/scanner parameters were recorded in the DICOM (digital imaging and communications in medicine) image header. For each slice, when applicable, two regions of interest (RoI) were extracted: one inside the femur and the other in the background. Based on the two RoIs, a SNR was calculated.

Figure 3:
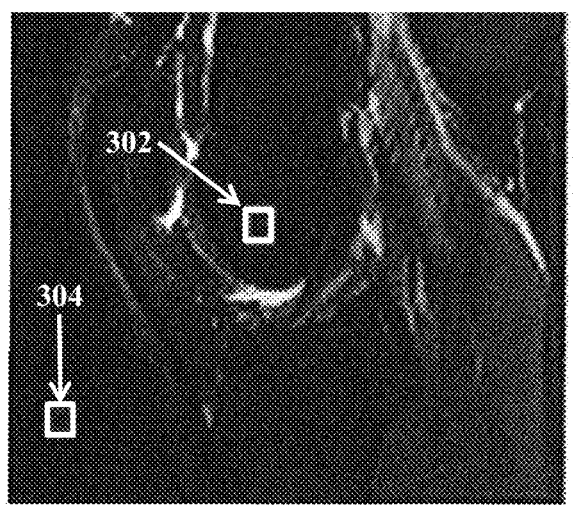
FIG. 3 shows an image slick of a femur having a region of interest in a femur and a region of interest outside of the femur, in accordance with one embodiment.

FIG. 3 illustratively depicts an image slice 300 of a femur, in accordance with one or more embodiments. RoI 302 is extracted from image slice 300 of a target structure (e.g., the femur) and RoI 304 is extracted from image slice 300 outside of the target structure (e.g., in the background). Based on the RoIs, a signal-to-noise ratio was calculated, where the signal component was calculated based on RoI 302 and the noise component was calculated based on RoI 304.

In one embodiment, SNR may be calculated according to equation (1).

$$SNR = \frac{\frac{1}{N_s}\sum_{i \in RoI_s} I_i}{\frac{1}{N_n}\sum_{j \in RoI_n} I_j}$$

Equation (1)

where $I_j$ is the intensity value of pixel j, $RoI_s$ and $RoI_n$ are the regions of interest for the signal (e.g., RoI 302) and noise (e.g., RoI 304) respectively, and $N_s$ and $N_n$ are the total number of pixels in $RoI_s$ and $RoI_n$ respectively. The average of all SNRs calculated from each slice in the same exam is used as the quality measure Q for the exam. For the same exam, the set of parameters {A} can be selected and retrieved from the DICOM header. In this experiment, the set of parameters {A} include the following parameters: repetition time (TR), echo time (TE), echo train length (ETL), fractional anisotropy (FA), slice thickness, pixel spacing, and bandwidth. As a result, each exam provided one training sample <{A}, Q>, and there are 38 samples in total. The regression model nu-SVR was applied to learn a mapping ϕ from {A} to Q.

Figure 4:
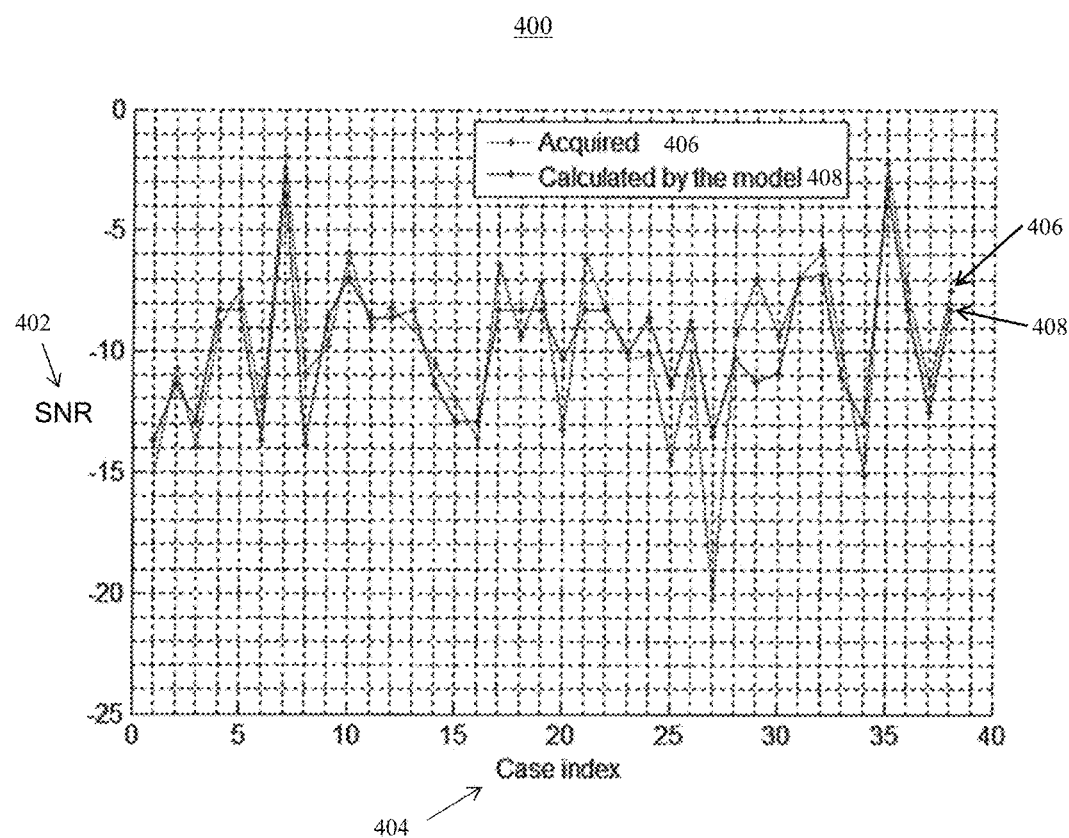
FIG. 4 shows a graph comparing an acquired signal-to-noise ratio and a calculated signal-to-noise ratio, in accordance with one embodiment.

FIG. 4 illustratively depicts a graph 400 comparing SNR 402 for each case index 404 (i.e., exams), in accordance with one or more embodiments. The acquired SNR 406 was determined for the training samples, e.g., by computing the SNR using equation (1). The calculated SNR 408 was calculated using the learned regression model ϕ. In particular, the learned regression model ϕ models the relationship between the parameters {A} and the quality metric Q. The learned regression model ϕ is a function that inputs the parameter set {A} and outputs the quality measure Q (in this case the SNR). Considering the presence of physiological noise in different exams, the learned regression model ϕ delivers reasonable predictions on the training set.

After mapping ϕ is learned, an interior point algorithm was used to solve an optimization problem: maximizing quality measure Q under mapping ϕ to determine optimized parameters {Â} which are constrained by the value range of the set of parameters {A}. The feasible value range for each parameter in the set of parameters {A} is provided in Table 1. The optimized parameters {Â} are determined as follows: [TR, TE, ETL, FA, Slice Thickness, Pixel Spacing, and Bandwidth]=[3653.5 31.6 10.0 175.7 3.0 0.7 231.4]. The optimal parameters {Â} are consistent with the experience of clinical experts regarding the relationship between the parameters and image quality. The DICOM tags used in Table 1 are from Siemens MR scanners.

TABLE 1 parameters in the set of parameters {A}

| Parameter | DICOM Tag | Value Range |
| --- | --- | --- |
| Repetition Time (TR) | <0018, 0080> | 2500-3800 |
| Echo Time (TE) | <0018, 0081> | 10-30 |
| Echo Train Length (ETL) | <0018, 0091> | 5-13 |
| Fractional Anisotropy (FA) | <0018, 1314> | 120-180 |
| Slice Thickness | <0018, 0050> | 3-4 |
| Pixel Spacing | <0028, 0030> | (256-512) 0.4-0.8 mm/pixel |
| Bandwidth | <0018, 0095> | Hertz/pixel: 130-300 |

Figure 5:
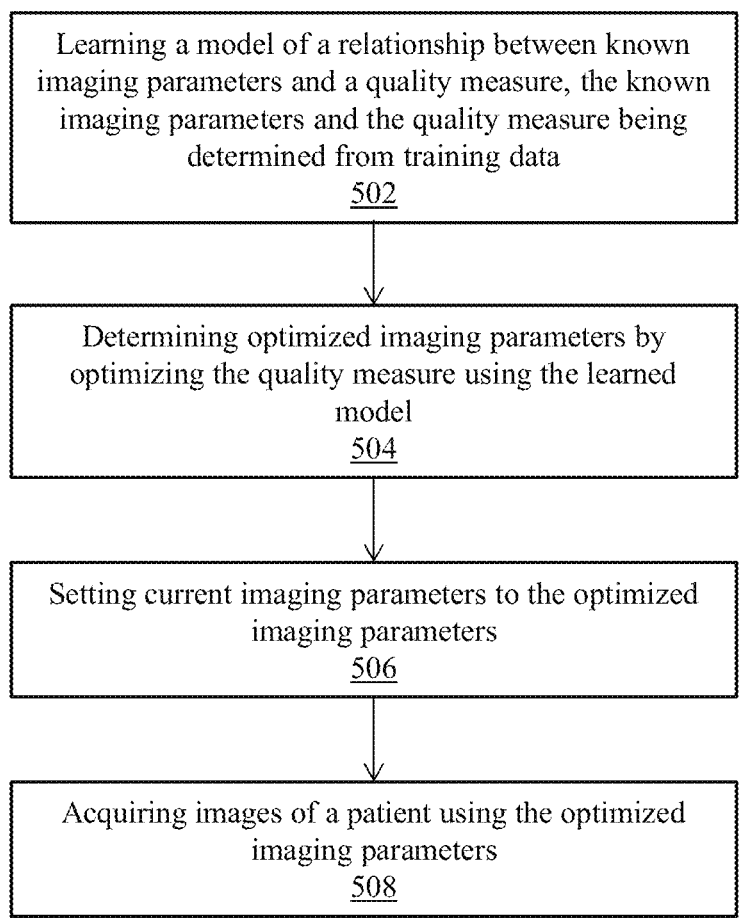
FIG. 5 shows a method for determining parameters for medical imaging, in accordance with one embodiment.

FIG. 5 shows a method 500 for determining parameters for medical imaging, in accordance with one or more embodiments. At step 502, a model or mapping ϕ is learned of a relationship between known imaging parameters {A} in training data and a quality measure Q in the training data. The model may be learned using any type of regression analysis, such as, e.g., SVR.

The training data may be acquired prior to a procedure and may include training images annotated with the known imaging parameters {A} and corresponding values for the quality measure Q. The known imaging parameters {A} may include imaging parameters for an image acquisition device, parameters of a subject or patient, parameters of the procedure, or any other parameter. The quality measure Q may be any measure or combination of measures representing the quality of images for a particular application and may be defined based on the procedure being performed. For example, the quality measure Q may be defined as a SNR, a CNR, a resolution, a measure of motion artifacts, a measure of ghosting, qualitative clinical diagnostic image quality measures, or any other suitable quality measure or combination of quality measures. In some embodiments, the quality measure Q may be selected or defined based on the procedure being performed.

In one embodiment, the quality measure Q is defined as the SNR. The SNR may be determined by defining a first region of interest in a target structure (e.g., the femur) of an image and a second region of interest outside of the target structure (e.g., in the background) of the image. The SNR may be determined as defined in equation (1). In particular, the SNR may be determined for each slice of a scan as the ratio between an average intensity value of pixels in the first region of interest and an average intensity value of pixels in the second region of interest. The SNR for each slice of the scan may then be averaged to get the SNR for the scan.

At step 504, optimized imaging parameters {Â} are determined by optimizing the quality measure Q using the learned model ϕ. The learned model ϕ models the relationship between the known imaging parameters {A} and the quality metric Q. The learned model ϕ is a function that inputs the set of known imaging parameters {A} and outputs a value of the quality measure Q. The quality measure Q may be optimized using any suitable algorithm, such as, e.g., an interior point algorithm. In one embodiment, optimizing the quality measure Q comprises finding the known image parameters {A} that maximizes the quality measure Q using the learned model ϕ.

At step 506, the current imaging parameters are set to the optimized imaging parameters. At step 508, medical images are acquired of a patient using the optimized imaging parameters. Advantageously, the medical images of the patient acquired using the optimized imaging parameters provide good quality images.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 5. Certain steps of the methods described herein, including one or more of the steps of FIG. 5, may be performed by a server or by another processor in a network-based cloud-computing system. Certain steps of the methods described herein, including one or more of the steps of FIG. 5, may be performed by a client computer in a network-based cloud computing system. The steps of the methods described herein, including one or more of the steps of FIG. 5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
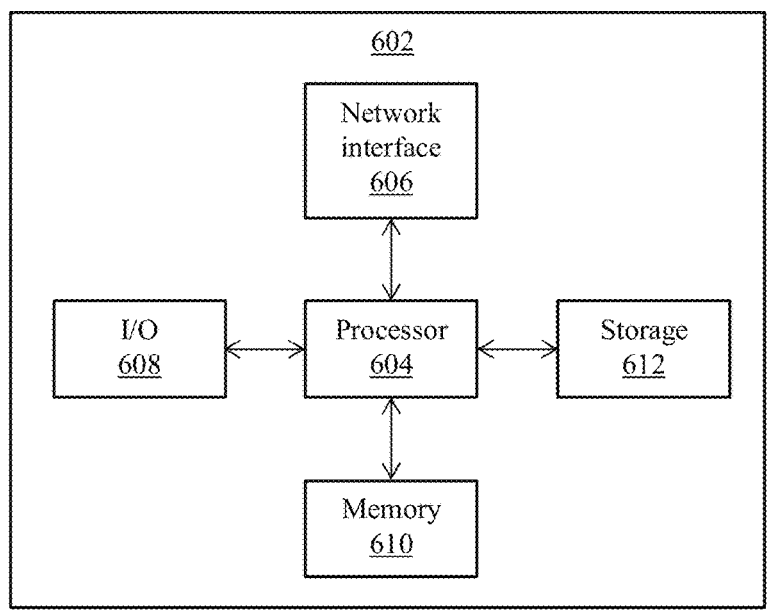
FIG. 6 shows a high-level block diagram of a computer for determining parameters for medical imaging, in accordance with one embodiment.

A high-level block diagram 600 of an example computer that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method steps of FIG. 5 can be defined by the computer program instructions stored in memory 610 and/or data storage device 612 and controlled by processor 604 executing the computer program instructions. For example, the computer program instructions can be implemented as computer executable code programmed by one skilled in the art to perform the method steps of FIG. 5 and the modules of workstation 102 of FIG. 1. Accordingly, by executing the computer program instructions, the processor 604 executes the method steps of FIG. 5 and modules of workstation 102 of FIG. 1. Computer 604 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 680 may include a display device such as a cathode ray tube (CRT) or liquid crystal display (LCD) monitor for displaying information to the user, a keyboard, and a pointing device such as a mouse or a trackball by which the user can provide input to computer 602.

Any or all of the systems and apparatus discussed herein, including elements of workstation 102 of FIG. 1, may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for determining optimized imaging parameters for imaging a patient, comprising:
   learning a model of a relationship between known imaging parameters and a quality measure, the known imaging parameters and the quality measure being determined from training data, wherein the quality measure is based on a signal-to-noise ratio (SNR) determined as a ratio between an average intensity value of pixels in a first region of interest in a target structure in an image and an average intensity value of pixels in a second region of interest outside of the target structure in the image;
   determining optimized imaging parameters by optimizing the quality measure using the learned model, the optimized imaging parameters comprising parameters of an image acquisition device and patient parameters for imaging the patient, the optimized imaging parameters being constrained to be within a range of the known imaging parameters; and
   acquiring images of the patient using the image acquisition device based on the optimized imaging parameters.

2. The method as recited in claim 1, wherein optimizing the quality measure using the learned model comprises maximizing the quality measure.

3. The method as recited in claim 1, wherein the quality measure is further based on an additional metric, the additional metric comprising at least one of a contrast-to-noise ratio, a resolution, a measure of motion artifacts, and a measure of ghosting.

4. The method as recited in claim 3, wherein the additional metric is selected based on a procedure being performed.

5. The method as recited in claim 1, wherein the known imaging parameters comprise parameters for operating the image acquisition device.

6. The method as recited in claim 1, wherein optimizing the quality measure comprises optimizing the quality measure using an interior point algorithm.

7. The method as recited in claim 1, wherein learning the model comprises learning the model using a regression analysis.

8. An apparatus for determining optimized imaging parameters for imaging a patient, comprising:
   means for learning a model of a relationship between known imaging parameters and a quality measure, the known imaging parameters and the quality measure being determined from training data, wherein the quality measure is based on a signal-to-noise ratio (SNR) determined as a ratio between an average intensity value of pixels in a first region of interest in a target structure in an image and an average intensity value of pixels in a second region of interest outside of the target structure in the image;
   means for determining optimized imaging parameters by optimizing the quality measure using the learned model, the optimized imaging parameters comprising parameters of an image acquisition device and patient parameters for imaging the patient, the optimized imaging parameters being constrained to be within a range of the known imaging parameters; and
   means for acquiring images of the patient using the optimized imaging parameters.

9. The apparatus as recited in claim 8, wherein the means for determining optimized imaging parameters by optimizing the quality measure using the learned model comprises means for maximizing the quality measure.

10. The apparatus as recited in claim 8, wherein the quality measure is further based on an additional metric, the additional metric comprising at least one of a contrast-to-noise ratio, a resolution, a measure of motion artifacts, and a measure of ghosting.

11. The apparatus as recited in claim 10, wherein the additional metric is selected based on a procedure being performed.

12. The apparatus as recited in claim 8, wherein the known imaging parameters comprise parameters for operating the image acquisition device.

13. The apparatus as recited in claim 8, wherein the means for optimizing the quality measure comprises means for optimizing the quality measure using an interior point algorithm.

14. The apparatus as recited in claim 8, wherein the means for learning the model comprises means for learning the model using a regression analysis.

15. A non-transitory computer readable medium storing computer program instructions for determining optimized imaging parameters for imaging a patient, the computer program instructions when executed by a processor cause the processor to perform operations comprising:
   learning a model of a relationship between known imaging parameters and a quality measure, the known imaging parameters and the quality measure being determined from training data, wherein the quality measure is based on a signal-to-noise ratio (SNR) determined as a ratio between an average intensity value of pixels in a first region of interest in a target structure in an image and an average intensity value of pixels in a second region of interest outside of the target structure in the image;
   determining optimized imaging parameters by optimizing the quality measure using the learned model, the optimized imaging parameters comprising parameters of an image acquisition device and patient parameters for imaging the patient, the optimized imaging parameters being constrained to be within a range of the known imaging parameters; and
   acquiring images of the patient using the optimized imaging parameters.

16. The non-transitory computer readable medium as recited in claim 15, wherein optimizing the quality measure using the learned model comprises maximizing the quality measure.

17. The non-transitory computer readable medium as recited in claim 15, wherein the quality measure is further based on an additional metric, the additional metric comprising at least one of a contrast-to-noise ratio, a resolution, a measure of motion artifacts, and a measure of ghosting.

18. The non-transitory computer readable medium as recited in claim 17, wherein the additional metric is selected based on a procedure being performed.

19. The non-transitory computer readable medium as recited in claim 15, wherein the known imaging parameters comprise parameters for operating the image acquisition device.

20. The non-transitory computer readable medium as recited in claim 15, wherein optimizing the quality measure comprises optimizing the quality measure using an interior point algorithm.

21. The non-transitory computer readable medium as recited in claim 15, wherein learning the model comprises learning the model using a regression analysis.

* * * * *